US009629652B2

(12) United States Patent
Mumaw et al.

(10) Patent No.: US 9,629,652 B2
(45) Date of Patent: Apr. 25, 2017

(54) SURGICAL INSTRUMENT WITH CLUTCHING SLIP RING ASSEMBLY TO POWER ULTRASONIC TRANSDUCER

(75) Inventors: Daniel J. Mumaw, Johannesburg (ZA); David A. Witt, Maineville, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 99 days.

(21) Appl. No.: 13/269,883

(22) Filed: Oct. 10, 2011

(65) Prior Publication Data

US 2013/0090675 A1    Apr. 11, 2013

(51) Int. Cl.
  *A61B 17/32*   (2006.01)
  *A61B 17/00*   (2006.01)
  *A61B 17/29*   (2006.01)

(52) U.S. Cl.
  CPC .... *A61B 17/320092* (2013.01); *A61B 17/00234* (2013.01); *A61B 2017/00477* (2013.01); *A61B 2017/291* (2013.01)

(58) Field of Classification Search
  CPC .... A61B 2017/00477; A61B 2017/291; A61B 2017/22014; A61B 2017/22015; A61B 2017/22021; A61B 2017/22027; A61B 17/320092; A61B 17/320068; A61B 17/00234; A61B 17/00238; A61C 3/03; A61F 9/00745
  USPC ......... 310/317, 365, 323.01, 323.02, 323.18, 310/322, 15, 22–24, 30, 12.01, 78, 128, 310/143–151; 439/919, 950, 259, 225; 606/40, 171, 1, 52, 51, 50, 34, 27; 604/22; 600/459
  See application file for complete search history.

(56) References Cited

U.S. PATENT DOCUMENTS 4,326,274 A * 4/1982 Hotta et al. .................. 367/118
5,980,510 A * 11/1999 Tsonton et al. .................. 606/1
(Continued)

FOREIGN PATENT DOCUMENTS

CN   200957109 Y   10/2007
CN   201101573 Y   8/2008
WO   WO 2011/008672   1/2011

OTHER PUBLICATIONS

U.S. Appl. No. 13/269,899, filed Oct. 10, 2011, Boudreaux et al.
(Continued)

*Primary Examiner* — Jocelin Tanner
(74) *Attorney, Agent, or Firm* — Frost Brown Todd LLC

(57) ABSTRACT

A surgical system includes a power supply, a connector, and a surgical instrument having a body assembly, a transmission assembly, a transducer, and a connection assembly. The connection assembly is configured to selectively electrically couple electrodes on the transducer with wires of the connector. The connection assembly may be operable in response to actuation of a trigger. Various connection assemblies include an extensible member that extends to contact an electrode, a rotatable member that rotates a contact into contact with an electrode, a solenoid that extends contacts coupled to each end of the solenoid into the electrodes, or a solenoid that translates a frame having contacts towards the electrodes. Alternatively, the surgical instrument may include a connection assembly having a slip ring and a weighted cable end. Still further, the connection assembly may include contacts on a coupleable member that may be decoupled from contacts on the transducer.

21 Claims, 10 Drawing Sheets

(56) References Cited

U.S. PATENT DOCUMENTS

| | | |
|---|---|---|
| 6,500,176 B1 | 12/2002 | Truckai et al. |
| 6,783,524 B2 | 8/2004 | Anderson et al. |
| 7,416,101 B2 | 8/2008 | Shelton, IV et al. |
| 7,738,971 B2 | 6/2010 | Swayze et al. |
| 8,418,349 B2 | 4/2013 | Smith et al. |
| 2004/0116952 A1* | 6/2004 | Sakurai et al. ............... 606/169 |
| 2006/0079874 A1* | 4/2006 | Faller et al. .................... 606/40 |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2009/0143797 A1 | 6/2009 | Smith et al. |
| 2009/0209990 A1 | 8/2009 | Yates et al. |
| 2010/0069940 A1 | 3/2010 | Miller et al. |
| 2011/0015660 A1 | 1/2011 | Wiener et al. |
| 2011/0087212 A1 | 4/2011 | Aldridge et al. |
| 2011/0087218 A1 | 4/2011 | Boudreaux et al. |

OTHER PUBLICATIONS

European Search Report dated Aug. 28, 2014 for Application No. EP 12188030.6, 7 pages.
Chinese Office Action dated Oct. 10, 2015 for Application No. CN 201210397423.2, 10 pages.
Japanese Office Action dated Jun. 21, 2016 for Application No. JP 2012-223858, 4 pages.

\* cited by examiner

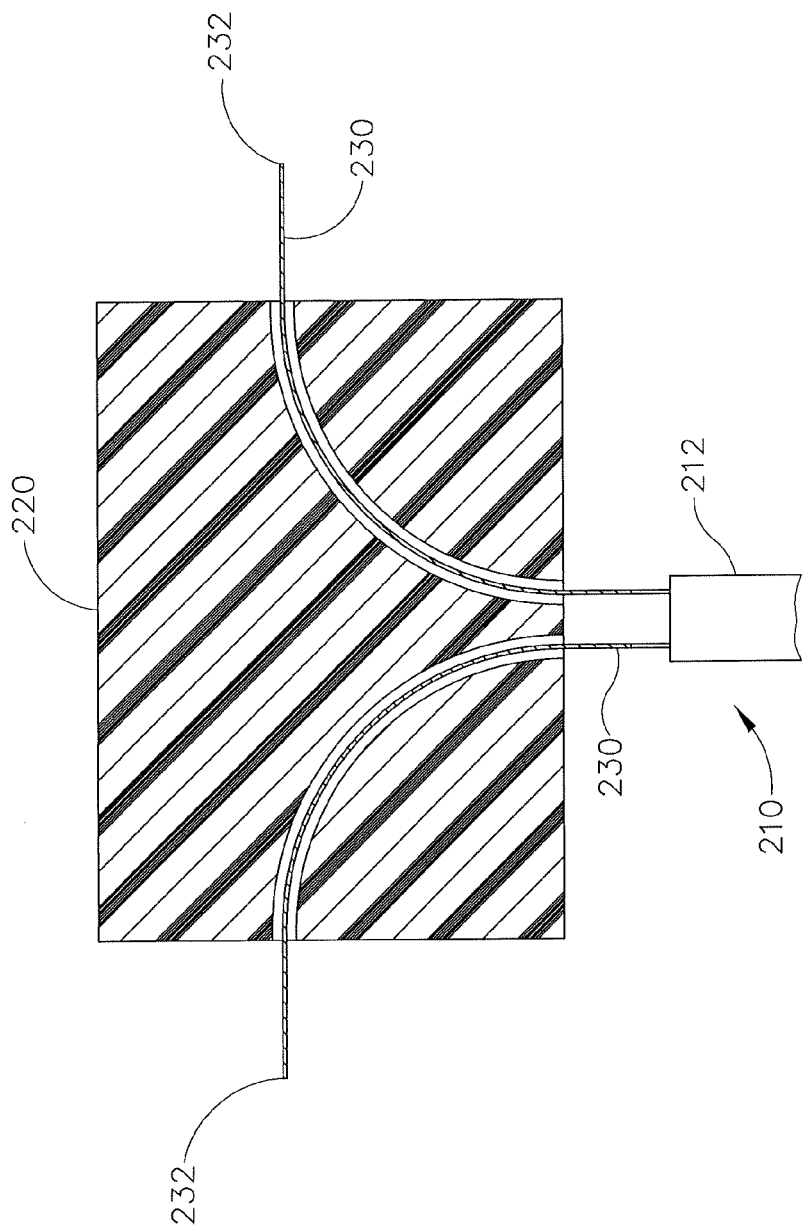

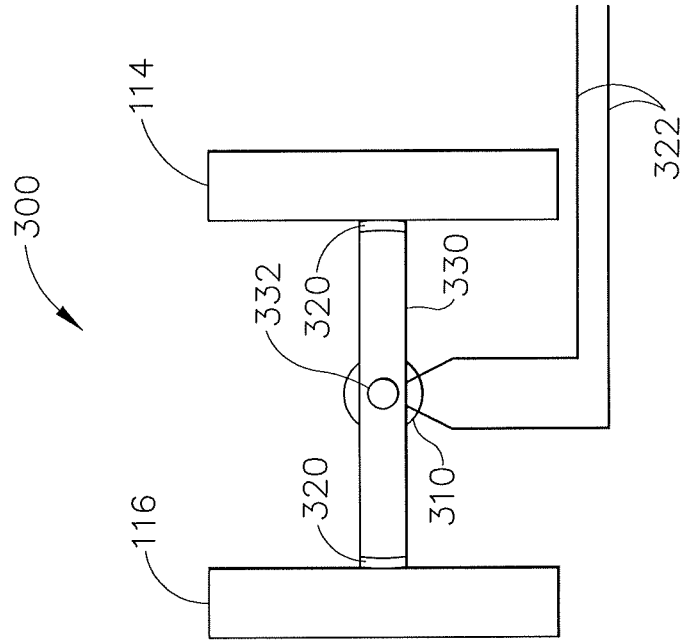
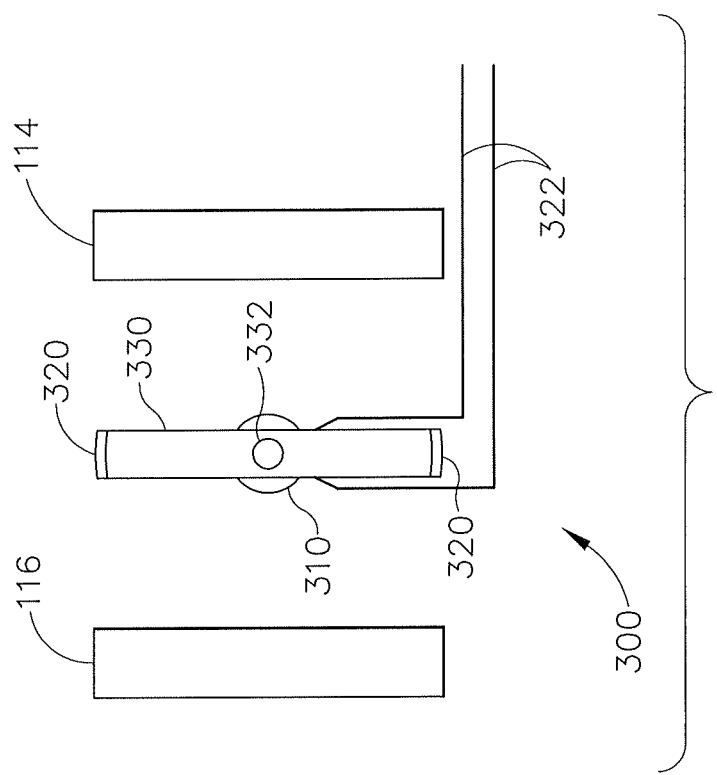
Fig. 5B
Fig. 5A

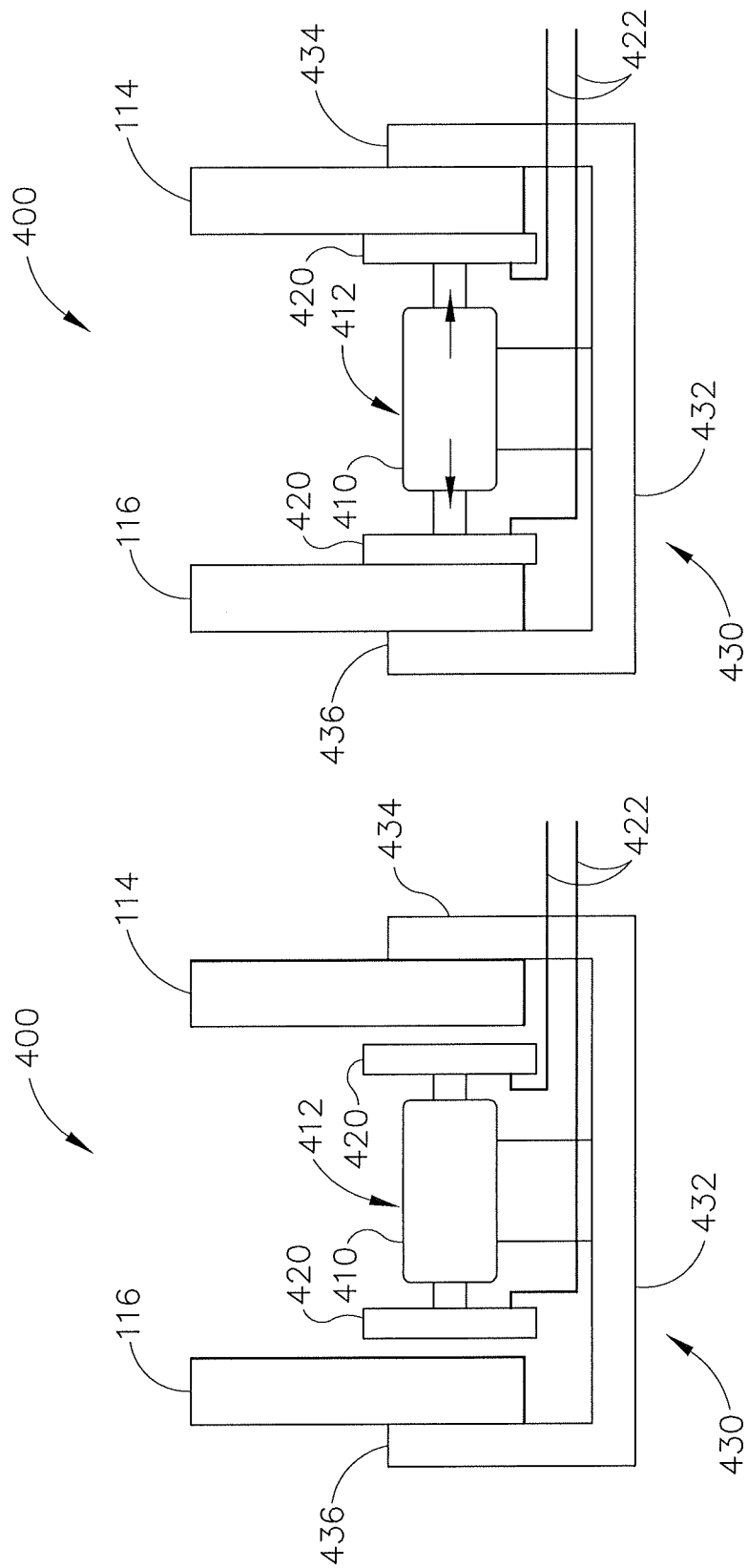

SURGICAL INSTRUMENT WITH CLUTCHING SLIP RING ASSEMBLY TO POWER ULTRASONIC TRANSDUCER

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient.

Examples of endoscopic surgical instruments include those disclosed in U.S. Pat. Pub. No. 2006/0079874, entitled "Tissue Pad for Use with an Ultrasonic Surgical Instrument," published Apr. 13, 2006, the disclosure of which is incorporated by reference herein; U.S. Pat. Pub. No. 2007/0191713, entitled "Ultrasonic Device for Cutting and Coagulating," published Aug. 16, 2007, the disclosure of which is incorporated by reference herein; U.S. Pat. Pub. No. 2007/0282333, entitled "Ultrasonic Waveguide and Blade," published Dec. 6, 2007, the disclosure of which is incorporated by reference herein; U.S. Pat. Pub. No. 2008/0200940, entitled "Ultrasonic Device for Cutting and Coagulating," published Aug. 21, 2008, the disclosure of which is incorporated by reference herein; U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; and U.S. Pat. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein. In addition, the surgical instruments may be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

While several systems and methods have been made and used for surgical instruments, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 4 depicts a cross-sectional view of an exemplary redirection member of the connection assembly of FIGS. 3A-3B;

FIG. 5A depicts an enlarged elevation view of another exemplary connection assembly using a rotatable member;

FIG. 5B depicts an enlarged elevation view of the connection assembly of FIG. 5A showing the rotation of the rotatable member to electrically couple to the electrodes;

FIG. 6A depicts an enlarged elevation view of yet another exemplary connection assembly using a solenoid to extend a pair of contacts;

FIG. 6B depicts an enlarged elevation view of the connection assembly of FIG. 6A showing the extension of the contacts to electrically couple to the electrodes;

Figure 1:
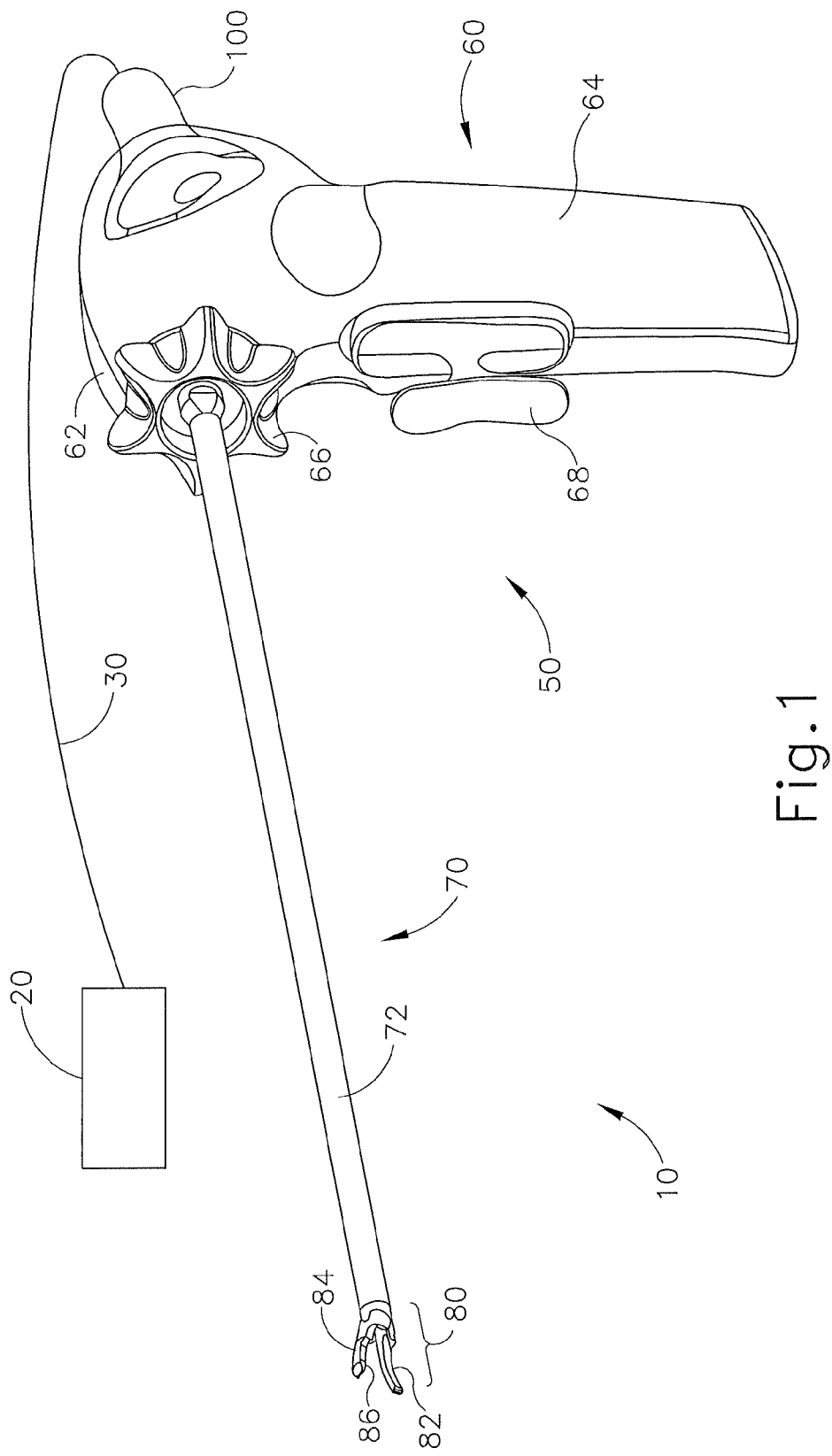
FIG. 1 depicts a perspective view of an exemplary surgical system having a surgical instrument and a generator.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Ultrasonic Surgical System

FIG. 1 shows an exemplary ultrasonic surgical system (10) comprising a surgical instrument (50), a generator (20), and a cable (30) coupling generator (20) to surgical instrument (50). A suitable generator (20) is the GEN 300 sold by Ethicon Endo-Surgery, Inc. of Cincinnati, Ohio. By way of example only, generator (20) may be constructed in accordance with the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should be noted that surgical instrument (50) will be described in reference to an ultrasonic surgical instrument; however, the technology described below may be used with a variety of surgical instruments, including, but not limited to, endocutters, graspers, cutters, staplers, clip appliers, access devices, drug/gene therapy delivery devices, and energy delivery devices using ultrasound, RF, laser, etc., and/or any combination thereof as will be apparent to one of ordinary skill in the art in view of the teachings herein. Moreover, while the present example will be described in reference to a cable-connected surgical instrument (50), it should be understood that surgical instrument (50) may be adapted for cordless operation Furthermore, surgical device (50) may also be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

Surgical instrument (50) of the present example includes a multi-piece handle assembly (60), an elongated transmission assembly (70), and a transducer (100). Transmission assembly (70) is coupled to multi-piece handle assembly (60) at a proximal end of transmission assembly (70) and extends distally from multi-piece handle assembly (60). In the present example transmission assembly (70) is configured to be an elongated, thin tubular assembly for endoscopic use, but it should be understood that transmission assembly (70) may alternatively be a short assembly, such as those disclosed in U.S. Pat. Pub. No. 2007/0282333, entitled "Ultrasonic Waveguide and Blade," published Dec. 6, 2007, and U.S. Pat. Pub. No. 2008/0200940, entitled "Ultrasonic Device for Cutting and Coagulating," published Aug. 21, 2008, the disclosures of which are incorporated by reference herein. Transmission assembly (70) of the present example comprises an outer sheath (72), an inner tubular actuating member (not shown), a waveguide (76), also shown best in FIG. 2, and an end effector (80) located on the distal end of transmission assembly (70). In the present example, end effector (80) comprises a blade (82) coupled to waveguide (76), a clamp arm (84) operable to pivot at the proximal end of transmission assembly (70), and, optionally, one or more clamp pads (86) coupleable to clamp arm (84).

Multi-piece handle assembly (60) of the present example comprises a mating housing portion (62) and a lower portion (64). Mating housing portion (62) is configured to receive transducer (100) at a proximal end of mating housing portion (62) and to receive the proximal end of transmission assembly (70) at a distal end of mating housing portion (62). A rotation knob (66) is shown in the present example to rotate transmission assembly (70) and transducer (100), but it should be understood that rotation knob (66) is merely optional. Mating housing portion (62) will be discussed in greater detail below in reference to FIG. 2. Lower portion (64) of multi-piece handle assembly (60) shown in FIG. 1 includes a trigger (68) and is configured to be grasped by a user using a single hand. One merely exemplary configuration for lower portion (64) is depicted in FIG. 1 of U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein. Toggle buttons (69), shown in FIG. 2 of the present disclosure, are located on a distal surface of lower portion (64) and are operable to activate transducer (100) at different operational levels using generator (20). For instance, a first toggle button (69) may activate transducer (100) at a maximum energy level while a second toggle button (69) may activate transducer (100) at a minimum, non-zero energy level. Of course, toggle buttons (69) may be configured for energy levels other than a maximum and/or minimum energy level as will be apparent to one of ordinary skill in the art in view of the teachings herein.

While multi-piece handle assembly (60) has been described in reference to two distinct portions (62, 64), it should be understood that multi-piece handle assembly (60) may be a unitary assembly with both portions (62, 64) combined. Multi-piece handle assembly (60) may alternatively be divided into multiple discrete components, such as a separate activation portion (operable either by a user's hand or foot) and a separate mating housing portion (62). Such an activation portion may be operable to activate transducer (100) and may be remote from mating housing portion (62). Multi-piece handle assembly (60) may be constructed from a durable plastic (such as polycarbonate or a liquid crystal polymer), ceramics, metals, and/or any other suitable material as will be apparent to one of ordinary skill in the art in view of the teachings herein. In some other versions, trigger (68) and/or toggle buttons (69) are omitted. For instance, instrument (50) may be operated as part of a robotic system. Other configurations for multi-piece handle assembly (60) will also be apparent to those of ordinary skill in the art in view of the teachings herein. By way of example only, surgical instrument (50) may be constructed in accordance with at least some of the teachings of U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660, issued as U.S. Pat. No. 8,461,744; U.S. Pat. No. 6,500,176; and/or U.S. Pat. Pub. No. 2011/0087218, issued as U.S. Pat. No. 8,939,974. Still other configurations for multi-piece handle assembly (60) will be apparent to those of ordinary skill in the art in view of the teachings herein.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

II. Exemplary Connection Assemblies for Ultrasonic Surgical Instrument

In some instances it may be useful to selectively couple the electrical connection from cable (30) to transducer (100). For instance, transducer (100) may need to be rotated multiple times during an operation. In such instances, if cable (30) is fixed relative to transducer (100), then cable (30) may wind around unnecessarily. Accordingly, it may be preferable to include an electrical coupling mechanism that is selectively coupleable to reduce or eliminate the likelihood of cable (30) twisting around. In addition, it may also be preferable to selectively couple cable (30) to transducer (100) and/or blade (82) of surgical instrument (50) are to be used. Such selective coupling may reduce the wear on the electrical connection assembly. Merely exemplary configurations for such connection assemblies are described below.

A. Exemplary Multi-Piece Handle Assembly

Figure 2:
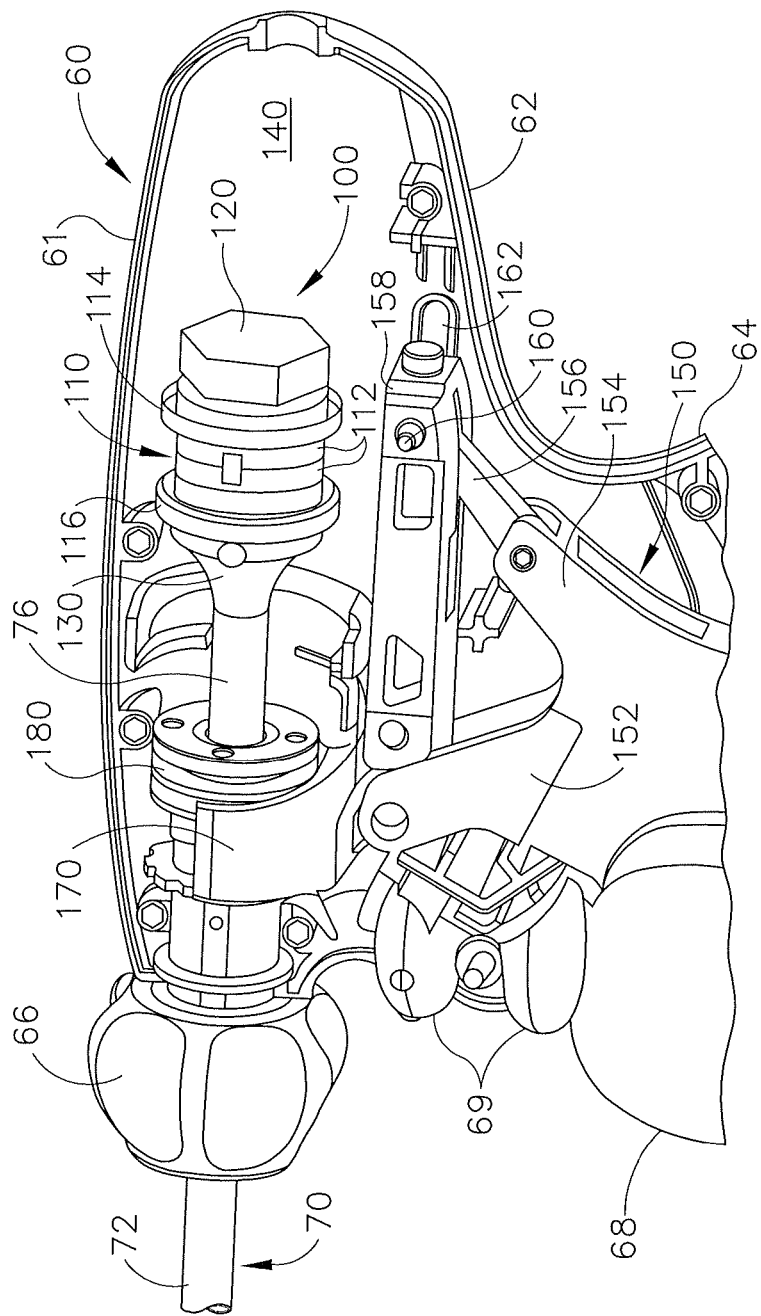
FIG. 2 depicts a partial side elevation view of an exemplary surgical instrument having a portion of a cover removed to show the interior of an exemplary multi-piece handle assembly.

FIG. 2 shows a partial side view of multi-piece handle assembly (60) with a portion of a cover (61) removed to show the internal components contained within mating housing portion (62) and a section of lower portion (64). As described above, lower portion (64) includes a pivotable trigger (68) and, optionally, a pair of toggle buttons (69). Trigger (68) of the present example is pivotable from a distal, open position to a proximal, closed position. A trigger assembly (150) is coupled to trigger (68) and is pivotally supported within multi-piece handle assembly (60). Trigger assembly (150) of the present example comprises a pivotable attachment arm (152) that may be pivoted about a pin (not shown), a trigger arm (154), an intermediate link (156), and an actuation arm (158). Actuation arm (158) is coupled to a trigger yoke (170) at the distal end of actuation arm (158). Actuation arm (158) comprises one or more mounting pins (160) extending outwardly from actuation arm (158) and pins (160) are sized to be slidably received in a corresponding elongated channel (162) formed in cover (61). Accordingly, when trigger (68) is pivoted proximally from the open position to the closed position, attachment arm (152) and trigger arm (154) pivot within multi-piece handle assembly (60). Intermediate link (156) coupled to trigger arm (154) transfers this pivoting motion from trigger arm (154) to actuation arm (158) to slidably translate actuation arm (158) proximally via pins (160) within channel (162). Trigger yoke (170), which is coupled to actuation arm (158), is translated proximally as well.

In the present example, trigger yoke (170) is coupled to a force-limiting mechanism (180) that is coupled to transmission assembly (70) to operate inner tubular actuating member (not shown) to thereby selectively pivot clamp arm (84). Merely exemplary configurations for transmission assembly (70), force limiting mechanism (180), trigger yoke (170), and transducer (100) are described in U.S. Pat. No. 9,050,125, entitled "Ultrasonic Surgical Instrument with Modular End Effector," issued on Jun. 9, 2015, the disclosure of which is incorporated by reference herein. It should also be understood that clamp arm (84) and associated features may be constructed and operable in accordance with at least some of the teachings of U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein. A cavity (140) is configured to receive at least a portion of transducer (100) (shown without an outer casing) therein such that transducer (100) and transmission assembly (70) may be coupled together within multi-piece handle assembly (60). Transducer (100) may be permanently encased within casing (61) or transducer (100) may be removable from cavity (140) through an aperture in casing (61). Still other configurations for multi-piece handle assembly (60) will be apparent to one of ordinary skill in the art in view of the teachings herein.

B. Exemplary Transducer

Still referring to FIG. 2, transducer (100) of the present example (shown without an outer casing) is coupleable to generator (20) via cable (30), though it should be understood that transducer (100) may be a cordless transducer having a power source contained within casing (61). In the present example, transducer (100) comprises a piezo stack assembly (110), a first resonator or end-bell (120), and a second resonator or fore-bell (130). In the present example, ultrasonic energy produced by transducer (100) is transmitted to blade (82) of end effector (80) via waveguide (76). Waveguide (76) is coupled at a proximal end to a horn (not shown) extending distally from second resonator (130). The horn may be fixedly coupled to waveguide (76) (such that rotation of transmission assembly (70) rotates transducer (100) and vice versa) or the horn may be configured to rotate freely relative to waveguide (76) (such that rotation of transmission assembly (70) is independent of transducer (100)).

In the present example, piezo stack assembly (110) comprises piezoelectric elements (112) that are compressed between first resonator (120) and second resonator (130) to form a stack of piezoelectric elements (112) when first resonator (120) and second resonator (130) are assembled with piezoelectric elements (112). Piezoelectric elements (112) may be fabricated from any suitable material, for example, lead zirconate-titanate, lead meta-niobate, lead titanate, and/or any suitable piezoelectric crystal material, for example. Piezo stack assembly (110) further comprises electrodes (114, 116), including at least one positive electrode (114) and at least one negative electrode (116) that are configured to create a voltage potential across the one or more piezoelectric elements (112). Of course, a plurality of electrodes (114, 116) and piezoelectric elements (112) may be stacked together as well. As shown in FIG. 2, positive electrode (114), negative electrode (116), and piezoelectric elements (112) can each be configured with a bore (not shown) to define a passageway that may receive a threaded portion of first resonator (120). In the example shown, positive electrode (114) and negative electrode (116) are annular rings, though it should be understood that other electrodes may be used, including linear projections, rings connectors coupled to an end of transducer (100), and/or any other suitable electrode or combination of electrodes as will be apparent to one of ordinary skill in the art in view of the teachings herein. One merely exemplary ultrasonic transducer (100) is Model No. HP054, sold by Ethicon Endo-Surgery, Inc. of Cincinnati, Ohio.

When transducer (100) of the present example is activated via toggle button (69) and/or trigger (68), transducer (100) is operable to create mechanical energy in the form of linear oscillations or vibrations (or other modes of vibration, e.g., torsional or transverse, etc.), at an ultrasonic frequency (such as 55.5 kHz). As shown, when transducer (100) is coupled to transmission assembly (70), then the oscillations are transmitted through waveguide (76) to end effector (80). In the present example, blade (82), being coupled to waveguide (76), thereby oscillates at the ultrasonic frequency. Thus, when tissue is secured between blade (82) and clamp arm (84), the ultrasonic oscillation of blade (82) may simultaneously sever the tissue and denature the proteins in adjacent tissue cells, thereby providing a coagulative effect with relatively little thermal spread. An electrical current may also be provided through blade (82) and clamp arm (84) to also cauterize the tissue. While some configurations for transducer (100) have been described, still other suitable configurations for transducer (100) will be apparent to one or ordinary skill in the art in view of the teachings herein.

C. Exemplary Extensible Connection Assembly

As noted previously, in some instances it may be useful to selectively couple and decouple the electrical connection between cable (30) and transducer (100). One merely exemplary connection assembly (200) includes one or more extensible members (230) to electrically couple power from generator (20) to transducer (100), as shown in FIGS. 3A-4. In the present example, connection assembly (200) comprises a solenoid (210), shown in FIG. 4, a redirection member (220), and a pair of extensible members (230). As shown in FIG. 4, redirection member (220) has a pair of arcuate passageways (222) formed therein and configured to redirect extensible members (230) at a 90 degree angle relative to solenoid (210). It should be understood, though, that other redirection angles for arcuate passageways (222) may be used, including any angle from zero degrees to 180 degrees. Redirection member (220) also comprises a non-conductive or insulating material, such that any contact by extensible members (230) with arcuate passageways (222) will not result in electrical coupling of redirection member (220) with extensible members (230). For instance, redirection member (220) may be a polymer or plastic member (such as polyethylene or PVC), a ceramic member, a glass member, and/or any other non-conductive or insulating member as will be apparent to one of ordinary skill in the art in view of the teachings herein. Alternatively, redirection member (220) may include a conductive material with the one or more arcuate passageways (222) being insulated with an insulating or non-conductive material. It should be understood that redirection member (220) may be electrically insulated through the use of a diode circuit and/or other electrical components, as will be apparent to one of ordinary skill in the art in view of the teachings herein. Still other configurations for redirection member (220) will be apparent to those of ordinary skill in the art in view of the teachings herein.

Extensible members (230) of the present example comprise resilient metallic strips such that extensible members (230) deform according to the path formed by arcuate passageways (222), but substantially return to a linear profile when not within arcuate passageways (222). Extensible members (230) may be made from copper, aluminium, gold, and/or any other conductive material as will be apparent to one of ordinary skill in the art in view of the teachings herein. Extensible members (230) include a second end (232) that is configured to contact and electrically couple to positive and/or negative electrode (114, 116) described above. For instance, second end (232) may include a flat plate (not shown) coupled thereto to provide a larger surface with which to contact positive or negative electrode (114, 116). Alternatively, thin brush members may be coupled to second end (232). Still other configurations for second end (232) will be apparent to one of ordinary skill in the art in light of the teachings herein. Extensible members (230) also include a first end which is coupled to a solenoid head (212) of solenoid (210). Solenoid head (212) may be a polymer or plastic member (such as polyethylene or PVC), a ceramic member, a glass member, and/or any other non-conductive or insulating member. Alternatively, in another version, solenoid head (212) may include a conductive material, but an insulated or non-conductive material may be provided between solenoid head (212) and extensible members (230). It should be understood that solenoid head (212) may be electrically insulated through the use of a diode circuit and/or other electrical components, as will be apparent to one of ordinary skill in the art in view of the teachings herein. Extensible members (230) are further electrically coupled to a positive and/or negative wire (218) that extends from cable (30) and from generator (20). In the present example, solenoid (210) is a linearly actuated solenoid moveable from a first position, in which extensible members (230) are retracted from electrical contact with positive and/or negative electrode (114, 116), shown in FIG. 3A; and a second position, in which extensible members (230) are extended to electrically couple with positive and/or negative electrode (114, 116), shown in FIG. 3B. Thus, when solenoid (210) is activated, power from generator (20) is electrically coupled to transducer (100) via positive and negative electrodes (114, 116) and extensible members (230).

Figure 3B:
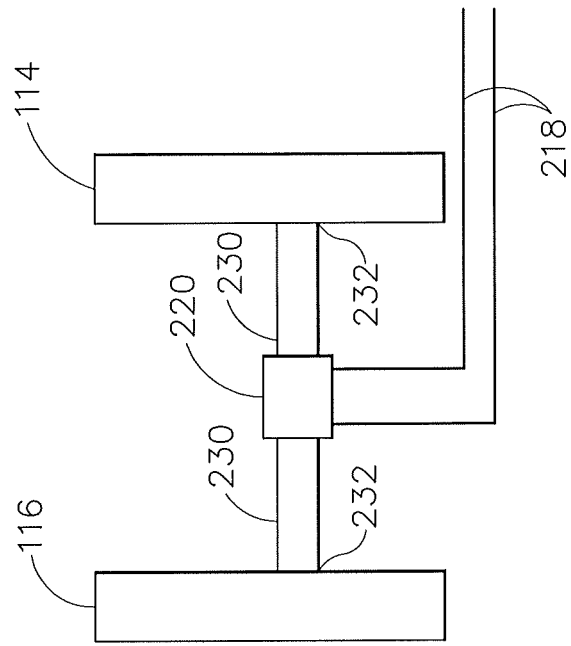
FIG. 3B depicts an enlarged elevation view of the connection assembly of FIG. 3A showing the extension of extensible members to electrically couple to electrodes of the transducer.
Figure 3A:
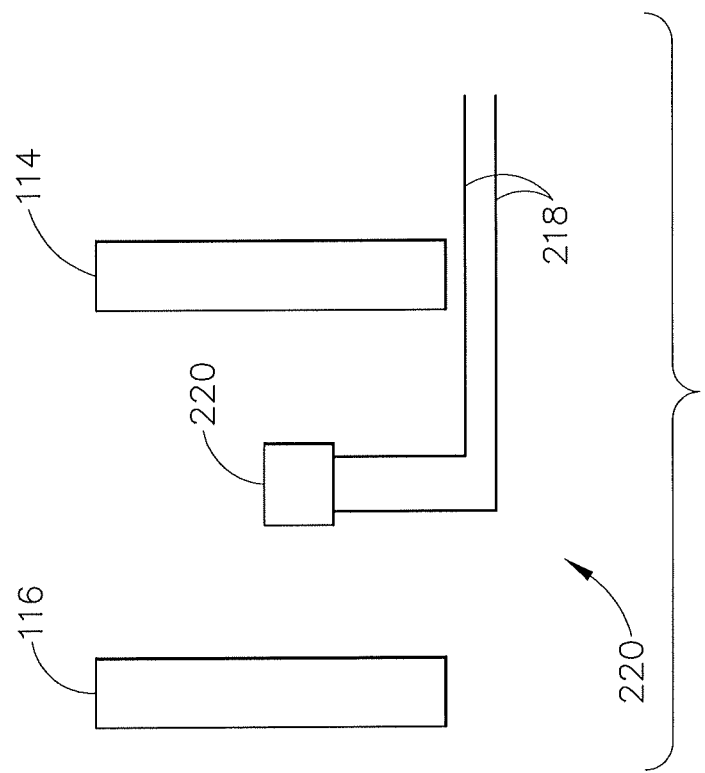
FIG. 3A depicts an enlarged elevation view of an exemplary connection assembly using a pair of extensible members.

In one merely exemplary version, connection assembly (200) may be configured to be in the first, retracted position, shown in FIG. 3A, when trigger (68) is not actuated, and such that connection assembly (200) extends to the second, extended position, shown in FIG. 3B, when trigger (68) (shown in FIGS. 1-2) is pulled. Such activation may be accomplished through a switch (not shown) to selectively apply power to solenoid (210) based upon the position of trigger (68). Accordingly, power may be selectively applied to transducer (100) via the coupling of extensible members (230) with positive and negative electrodes (114, 116) when solenoid (210) is activated in response to the user actuating trigger (68). Alternatively, solenoid (210) may be activated by toggle button (69) (shown in FIG. 2) and/or by any other activation device as will be apparent to one of ordinary skill in the art in view of the teachings herein.

Thus, transducer (100) may freely rotate relative to casing (61) and/or cable (30) while extensible members (230) are not extended, thereby potentially reducing the wear on extensible members (230) and also potentially avoiding tangling cable (30) when transducer (100) and/or transmission assembly (70) are rotated. Transducer (100) may still be rotatable when extensible members (230) are contacting positive and negative electrodes (114, 116). Still other configurations for connection assembly (200) will be apparent to one of ordinary skill in the art in view of the teachings herein. For instance, in some versions redirection member (220) may be omitted and extensible members (230) may be coupled to a single, dual action solenoid configured to extend outwardly to electrically couple extensible members (230) with positive and negative electrodes (114, 116). Alternatively, a pair of solenoids may be used instead of a single dual acting solenoid. In some other versions, trigger (68) may be mechanically coupled to extensible members (230) such that actuation of trigger (68) extends extensible members (230). In yet another alternative, a motor may be used to extend extensible members (230) instead of solenoid (210).

D. Exemplary Rotatable Connection Assembly

Another exemplary connection assembly (300) includes one or more rotatable members (330) to electrically couple power from generator (20) to transducer (100), as shown in FIGS. 5A-5B. In the present example, connection assembly (300) comprises a solenoid (310) and a rotatable member (330) having a pair of contacts (320). As shown in FIG. 5A, rotatable member (330) comprises a rectangular plate rotatable member having a pair of contacts (320) disposed at opposite ends. Rotatable member (330) also comprises a non-conductive or insulating material, such that contacts (320) are electrically isolated relative to the exterior of rotatable member (330) and the other contact (320). For instance, rotatable member (330) may be made from a polymer or plastic member (such as polyethylene or PVC), a ceramic member, a glass member, and/or any other non-conductive or insulating member as will be apparent to one of ordinary skill in the art in view of the teachings herein. Of course it should be understood that rotatable member (330) may be electrically insulated through the use of a diode circuit and/or other electrical components, as will be apparent to one of ordinary skill in the art in view of the teachings herein. Alternatively, in another version, rotatable member (330) may include a conductive material with an insulating or non-conductive material to isolate contacts (320) relative to one another and to rotatable member (330). By way of example only, rotatable member (330) may comprise a printed circuit board (PCB) portion having a first conductive trace (not shown) coupled to a positive contact (320) and a second conductive trace (not shown) corresponding to the negative contact (320), with the first and second conductive traces insulated relative to one another. Contacts (320) of the present example comprise a brush portion to electrically couple contact (320) with positive and/or negative electrodes (114, 116), as shown in FIG. 5B. Contacts (320) may be made from copper, aluminium, gold, and/or any other conductive material as will be apparent to one of ordinary skill in the art in view of the teachings herein. Of course other contacts (320) may be used, including resilient conductive tabs, plate contacts, inductive components, and/or any other suitable contact as will be apparent to one of ordinary skill in the art in view of the teachings herein. Contacts (320) are further electrically coupled to a positive and/or negative wire (322) that extends from cable (30). Wires (322) are insulated relative to each other and, in the present example, electrically couple to the conductive traces substantially near a midpoint (332) of rotatable member (330). Such electrical coupling from wires (322) to conductive traces may be accomplished via a direct soldered connection, a slip-ring connection, and/or any other suitable connection. Still other configurations for rotatable member (330) and/or contacts (320) will be apparent to those of ordinary skill in the art in view of the teachings herein.

Solenoid (310) of the present example is coupled at the midpoint (332) of rotatable member (330), and solenoid (310) is operable to rotate rotatable member (330). For instance, rotatable member (330) may be rotated to a 90 degree angle when solenoid (310) is activated, as shown in FIG. 5B, and may return to a 0 degree angle when solenoid (310) is inactive, as shown in FIG. 5A. Solenoid (310) may be a rotary solenoid or, in one alternative, a linear solenoid may be used with gearing (not shown), such as rack and pinion gears, to effect rotational motion to rotatable member (330). Alternatively, piezoelectric elements, motors (e.g., stepper motors), direct mechanical coupling to trigger (68), and/or any other suitable device may be used to rotate rotatable member (330) as will be apparent to one of ordinary skill in the art in view of the teachings herein. In the present example, when solenoid (310) is in inactive, shown in FIG. 5A, rotatable member (330) is vertical, or at a 0 angle, and contacts (320) are not electrically coupled with positive or negative electrode (114, 116). Once solenoid (310) is activated, shown in FIG. 5B, rotatable member (330) rotates 90 degrees such that contacts (320) electrically couple to positive and negative electrode (114, 116). Thus, when solenoid (310) is activated, power from generator (20) is electrically coupled to transducer (100) via positive and negative electrodes (114, 116) and contacts (320).

In one merely exemplary version, connection assembly (300) may be configured to be in the first position, shown in FIG. 5A, when trigger (68) is not actuated, and such that connection assembly (300) rotates rotatable member (330) to the second position, shown in FIG. 5B, when trigger (68) (shown in FIGS. 1-2) is pulled. Such activation may be accomplished through a switch (not shown) to selectively apply power to solenoid (310) based upon the position of trigger (68). Accordingly, power may be selectively applied to transducer (100) via the coupling of contacts (320) with positive and negative electrodes (114, 116) when solenoid (310) is activated in response to the user actuating trigger (68). Alternatively, solenoid (310) may be activated by toggle button (69) (shown in FIG. 2) and/or by any other activation device as will be apparent to one of ordinary skill in the art in view of the teachings herein.

Thus, transducer (100) may freely rotate relative to casing (61) and/or cable (30) while contacts (320) of rotatable member (330) are not rotated into an electrically coupled position, thereby reducing the potential wear on contacts (320) and/or rotatable member (330). Connection assembly (300) may also potentially avoid any tangling cable (30) when transducer (100) and/or transmission assembly (70) are rotated. Transducer (100) may still be rotate relative to casing (61) and/or cable (30) when contacts (320) contact positive and negative electrodes (114, 116). Of course, still other configurations for connection assembly (300) will be apparent to one of ordinary skill in the art in view of the teachings herein.

E. Exemplary Alternative Extensible Connection Assembly

Yet another exemplary connection assembly (400) includes one or more contacts (420) to electrically couple power from generator (20) to transducer (100), as shown in FIGS. 6A-6B. In the present example, connection assembly (400) comprises a solenoid (410), a pair of contacts (420), and a frame (430). Frame (430) of the present example comprises a base portion (432), a first end plate (434), and a second end plate (436). First and second end plates (434, 436) extend perpendicular from base portion (432) and are configured to extend beyond an end of positive and negative electrode (114, 116), as shown in FIGS. 6A-6B. Frame (430) comprises a non-conductive or insulating material, such that any contact by contacts (420) and/or wires (422) with base portion (432), first end plate (434), and/or second end plate (436) will not result in electrical coupling of frame (430) with contacts (420) and/or wires (422). For instance, frame (430) may be a polymer or plastic member (such as polyethylene or PVC), a ceramic member, a glass member, and/or any other non-conductive or insulating member as will be apparent to one of ordinary skill in the art in view of the teachings herein. Of course it should be understood that frame (430) may be electrically insulated through the use of a diode circuit and/or other electrical components, as will be apparent to one of ordinary skill in the art in view of the teachings herein. Still other configurations for frame (430) will be apparent to those of ordinary skill in the art in view of the teachings herein.

In the present example, solenoid (410) is disposed between a pair of contacts (420). Contacts (420) of the present example comprise metallic plates configured to electrically couple with positive and/or negative electrode (114, 116) when contacts (420) contact positive and/or negative electrode (114, 116). Contacts (420) may be made from copper, aluminium, gold, and/or any other conductive material as will be apparent to one of ordinary skill in the art in view of the teachings herein. Alternatively, thin brush members may be coupled to contacts (420) to couple to positive and/or negative electrode (114, 116). Still other configurations for contacts (420) will be apparent to one of ordinary skill in the art in light of the teachings herein. Contacts (420) are coupled to insulated solenoid heads of solenoid (410) such that any electricity applied to solenoid (410) is insulated relative to contacts (420) and such that each contact (420) is insulated relative to the other. The solenoid heads may include a polymer or plastic member (such as polyethylene or PVC), a ceramic member, a glass member, and/or any other non-conductive or insulating member. Of course it should be understood that the solenoid heads may be electrically insulated through the use of a diode circuit and/or other electrical components, as will be apparent to one of ordinary skill in the art in view of the teachings herein. Contacts (420) are each further electrically coupled to a positive and/or negative wire (422) that extends from cable (30).

In the present example, solenoid (410) is a dual-acting linearly actuated solenoid moveable from a first position, in which contacts (420) are retracted from positive and/or negative electrode (114, 116), shown in FIG. 6A, to a second position, in which contacts (420) are extended to electrically couple with positive and/or negative electrode (114, 116), shown in FIG. 6B. In the present example, a central portion (412) of solenoid (410) is fixed relative to frame (430) such that the ends of solenoid (410) extend outwardly from central portion (412). As shown in FIGS. 6A-6B, when contacts (420) are extended outwardly relative to central portion (412) of solenoid (410), contacts (420) compress positive and/or negative electrodes (114, 116) against first and/or second end plate (434, 436). Thus, a caliper brake-type compression of positive and/or negative electrodes (114, 116) may ensure electrical coupling of contacts (420) with positive and/or negative electrodes (114, 116). It should be understood that the compression need not be a high compression that will prevent rotation of transducer (100) when positive and/or negative electrodes (114, 116) are in contact with contacts (420) and first and/or second end plate (434, 436). As is readily apparent, when solenoid (410) is activated, power from generator (20) is electrically coupled to transducer (100) via positive and negative electrodes (114, 116) and contacts (420). Of course, alternative configurations for frame (430), contacts (420), and solenoid (410) will be apparent to one of ordinary skill in the art in view of the teachings herein. For instance, solenoid (410) may be affixed at one end and may be configured to compress a single contact (420) against either positive or negative electrode (114, 116). A second solenoid (410) and single contact (420) may be provided for the other electrode (114, 116). Still further, solenoid (410) may be positioned at one end of a scissor-style linkage with contacts (420) coupled to the opposite end of the scissor style linkage. Thus, when solenoid (410) extends outwardly against the first end of the scissor-style linkage, the opposite end of the scissor-style linkage also expands to compress positive and/or negative electrode (114, 116) against first and/or second end plate (434, 436). Of course such alternatives are merely exemplary.

In the example shown, connection assembly (400) is configured to be in the first, retracted position, shown in FIG. 6A, when trigger (68) is not actuated, and such that connection assembly (400) extends to the second, extended position, shown in FIG. 6B, when trigger (68) (shown in FIGS. 1-2) is pulled by a user. Such activation may be accomplished through a switch (not shown) to selectively apply power to solenoid (410) based upon the position of trigger (68). Accordingly, power may be selectively applied to transducer (100) via the coupling of contacts (420) with positive and negative electrodes (114, 116) when solenoid (410) is activated in response to the user actuating trigger (68). Alternatively, solenoid (410) may be activated by toggle button (69) (shown in FIG. 2) and/or by any other activation device as will be apparent to one of ordinary skill in the art in view of the teachings herein.

Thus, transducer (100) may freely rotate relative to casing (61) and/or cable (30) while contacts (420) are not compressed against positive or negative electrodes (114, 116), thereby potentially reducing the wear on contacts (420) and also potentially avoiding tangling cable (30) when transducer (100) and/or transmission assembly (70) are rotated. Transducer (100) may still rotate relative to casing (61) and/or cable (30) when contacts (420) contact positive and negative electrodes (114, 116). Of course, still other configurations for connection assembly (400) will be apparent to one of ordinary skill in the art in view of the teachings herein. For instance, contacts (420) may be rotated into compressive contact with electrodes (114, 116) in a similar manner to connection assembly (300) described above. It should be understood that solenoid (410) may be omitted and contacts (420) may be driven outwardly via a mechanical assembly (e.g., a wedge driven between contacts (420), etc.) that is directly coupled to trigger (68).

F. Exemplary Translatable Connection Assembly

Figure 7A:
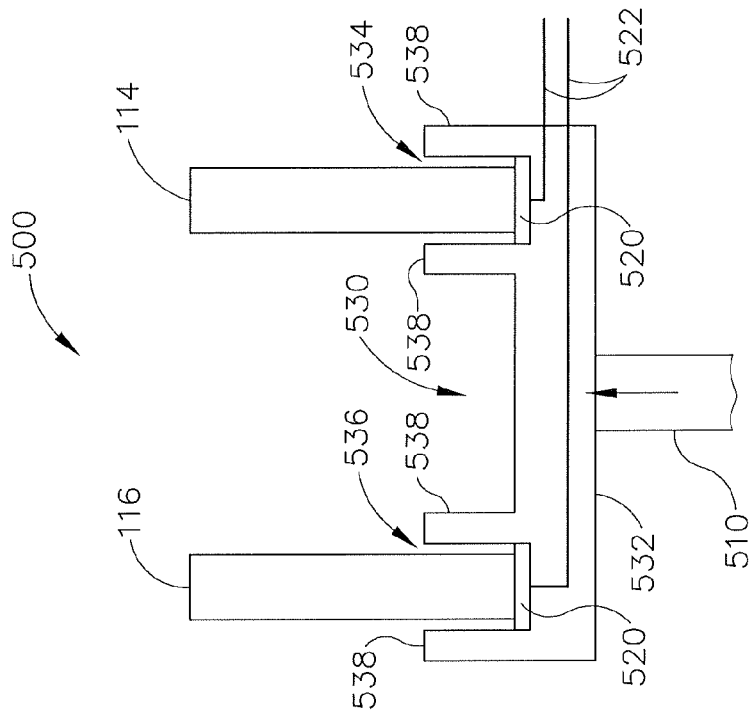
FIG. 7A depicts an enlarged elevation view of an exemplary alternative connection assembly using a translatable frame.
Figure 7B:
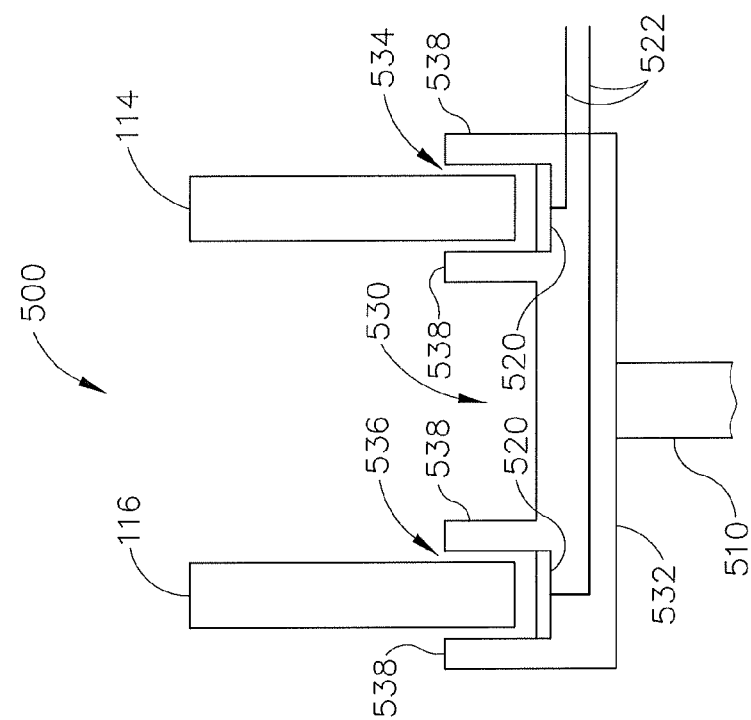
FIG. 7B depicts an enlarged elevation view of the connection assembly of FIG. 7A showing the translation of the frame and contacts to electrically couple to the electrodes.

Still another exemplary connection assembly (500) includes one or more contacts (520) to electrically couple power from generator (20) to transducer (100), as shown in FIGS. 7A-7B. In the present example, connection assembly (500) comprises a solenoid (510), a pair of contacts (520), and a frame (530) coupled to solenoid (510). Frame (530) of the present example comprises a base portion (532), a first contact recess (534), and a second contact recess (536). First and second contact recesses (534, 536) are each defined by a pair of walls (538) extending perpendicularly from base portion (532) to form a U shaped channel sized to receive an end of positive and/or negative electrode (114, 116), as shown in FIGS. 7A-7B. Frame (530) comprises a non-conductive or insulating material, such that contact by contacts (520) and/or wires (522) with base portion (532) and/or walls (538) will not result in electrical coupling of frame (530) with contacts (520) and/or wires (522). For instance, frame (530) may be a polymer or plastic member (such as polyethylene or PVC), a ceramic member, a glass member, and/or any other non-conductive or insulating member as will be apparent to one of ordinary skill in the art in view of the teachings herein. Of course it should be understood that frame (530) may be electrically insulated through the use of a diode circuit and/or other electrical components, as will be apparent to one of ordinary skill in the art in view of the teachings herein. Still other configurations for frame (530) will be apparent to those of ordinary skill in the art in view of the teachings herein.

In the present example, contacts (520) comprise metallic plates located within first and second contact recesses (534, 536) and are configured to electrically couple with positive and/or negative electrode (114, 116) when contacts (520) contact positive and/or negative electrode (114, 116). Contacts (520) may be made from copper, aluminium, gold, and/or any other conductive material as will be apparent to one of ordinary skill in the art in view of the teachings herein. Alternatively, thin brush members may be coupled to contacts (520) to couple to positive and/or negative electrode (114, 116). Still other configurations for contacts (520) will be apparent to one of ordinary skill in the art in light of the teachings herein. In one merely alternative version, frame (530), first and second contact recesses (534, 536), and contacts (520) may be arcuate members corresponding to the curvature of positive and negative electrodes (114, 116) (shown in FIG. 2). Contacts (520) of the present example are each further electrically coupled to a positive and/or negative wire (522) that extends from cable (30).

In the present example, solenoid (510) is coupled to frame (530) on a side opposite to first and second contact recesses (534, 536) and contacts (520). Solenoid (510) is a linearly actuated solenoid moveable from a first position, in which contacts (520) on frame (530) are retracted from electrical contact with positive and/or negative electrode (114, 116), shown in FIG. 7A, to a second position, in which contacts (520) on frame (530) are extended to electrically couple with positive and/or negative electrode (114, 116), shown in FIG. 7B. In the present example, a single solenoid (510) is fixed relative to frame (530) such that the end of solenoid (510) is extendible upwardly to translate frame (530) upwardly as well. As shown in FIGS. 7A-7B, when solenoid (510) is activated, frame (530) is translated upwardly such that contacts (520) electrically couple to positive and/or negative electrodes (114, 116). Accordingly, when solenoid (510) is activated, power from generator (20) is electrically coupled to transducer (100) via positive and negative electrodes (114, 116) and contacts (520). It should be understood that frame (530) may be translated by solenoid (510) in other directions as well, including sideways, downwardly, or in any other suitable direction (e.g., based on the locations of contact (520)). Of course, alternative configurations for frame (530), contacts (520), and solenoid (510) will be apparent to one of ordinary skill in the art in view of the teachings herein. For instance, solenoid (510) may be affixed to a single frame (530) and/or contact (520) to electrically couple contact (520) with either positive or negative electrode (114, 116). A second solenoid (510) and single contact (520) may be provided for the other electrode (114, 116). Still further, more than one solenoid (510) may be coupled to frame (530) and may be positioned such that each solenoid (510) is below, and opposite to, each contact (520). Of course such alternatives are merely exemplary.

In the example shown, connection assembly (500) is configured to be in the first, retracted position, shown in FIG. 7A, when trigger (68) is not actuated, and such that connection assembly (500) extends to the second, extended position, shown in FIG. 7B, when trigger (68) (shown in FIGS. 1-2) is pulled by a user. Such activation may be accomplished through a switch (not shown) to selectively apply power to solenoid (510) based upon the position of trigger (68). Accordingly, power may be selectively applied to transducer (100) via the coupling of contacts (520) with positive and negative electrodes (114, 116) when solenoid (510) is activated in response to the user actuating trigger (68). Alternatively, solenoid (510) may be activated by toggle button (69) (shown in FIG. 2) and/or by any other activation device as will be apparent to one of ordinary skill in the art in view of the teachings herein.

Thus, transducer (100) may freely rotate relative to casing (61) and/or cable (30) while contacts (520) are not compressed against positive or negative electrodes (114, 116), thereby potentially reducing the wear on contacts (520) and also potentially avoiding tangling cable (30) when transducer (100) and/or transmission assembly (70) are rotated. Transducer (100) may still rotate relative to casing (61) and/or cable (30) when contacts (520) contact positive and negative electrodes (114, 116). Of course, still other configurations for connection assembly (500) will be apparent to one of ordinary skill in the art in view of the teachings herein. For instance, trigger (68) may be mechanically coupled to frame (530) such that actuation of trigger (68) extends frame (530) into contact with electrodes (114, 116). In yet another alternative, a motor may be used to extend frame (530) instead of solenoid (510).

It should be understood that at least portions of the foregoing connection assemblies (200, 300, 400, 500) may be contained within the outer casing of transducer (100). In addition, or in the alternative, at least portions of connection assemblies (200, 300, 400, 500) may be within mating housing portion (62) of surgical instrument (50) and configured to couple to positive and negative electrodes (114, 116) extending out of outer casing of transducer (100). Further still, the foregoing connection assemblies (200, 300, 400, 500) may be configured to actuate away from positive and negative electrodes (114, 116) in response to an ejection button (not shown) such that a removable transducer (100) may be removed from within mating housing portion (62) without catching on connection assemblies (200, 300, 400, 500). In addition, while the foregoing connection assemblies (200, 300, 400, 500) describe the activation of solenoids or other devices in response to trigger (68) and/or toggle buttons (69), it should be understood that a separate button may be included to activate solenoids or etc. As another merely illustrative example, a signal from generator (20) may activate solenoids, etc. in response to a separate signal (such as a signal indicating trigger (68) has been actuated).

Moreover, it should be understood that features from one connection assembly (200, 300, 400, 500) may be combined with a different connection assembly (200, 300, 400, 500). For instance, connection assembly (500) that translates frame (530) upwardly toward positive and negative electrodes (114, 116) may be used with connection assembly (400) with a second solenoid (410) to couple contacts (420) (which replace the internally located sidewalls (538)) with positive and negative electrodes (114, 116). Thus, a pair of solenoids (510, 410) may both actuate frame (530) and electrically couple contacts (420) with positive and negative electrodes (114, 116). Additionally, a rotational and extensible combination may be created by combining features of connection assembly (200) with connection assembly (300). Further still, connection assembly (500) may be combined with connection assembly (200) and/or connection assembly (300) to provide a translatable frame with extensible members (230) and/or rotatable members (330). Moreover, a plurality of connection assemblies (200, 300, 400, 500) may be combined for redundancy and/or reliability purposes as well. Still other configurations will be apparent to one of ordinary skill in the art in view of the teachings herein.

G. Exemplary Slip Ring With Weighted Cable End

In some instances it may be useful to provide a rotatable electrical connection from cable (30) to transducer (100). For instance, in some instances transducer (100) may need to be rotated relative to casing (61) multiple times during an operation. In these instances, if cable (30) is fixed relative to transducer (100), cable (30) may wind around unnecessarily. Accordingly, it may be preferable to include a rotatable electrical connection between a cable end and transducer (100) to reduce or eliminate the likelihood of cable (30) twisting around when transducer (100) is rotated. In other words, it may be desirable to permit transducer (100) to rotate relative to cable (30) while still maintaining electrical continuity between transducer (100) and cable (30).

Figure 8:
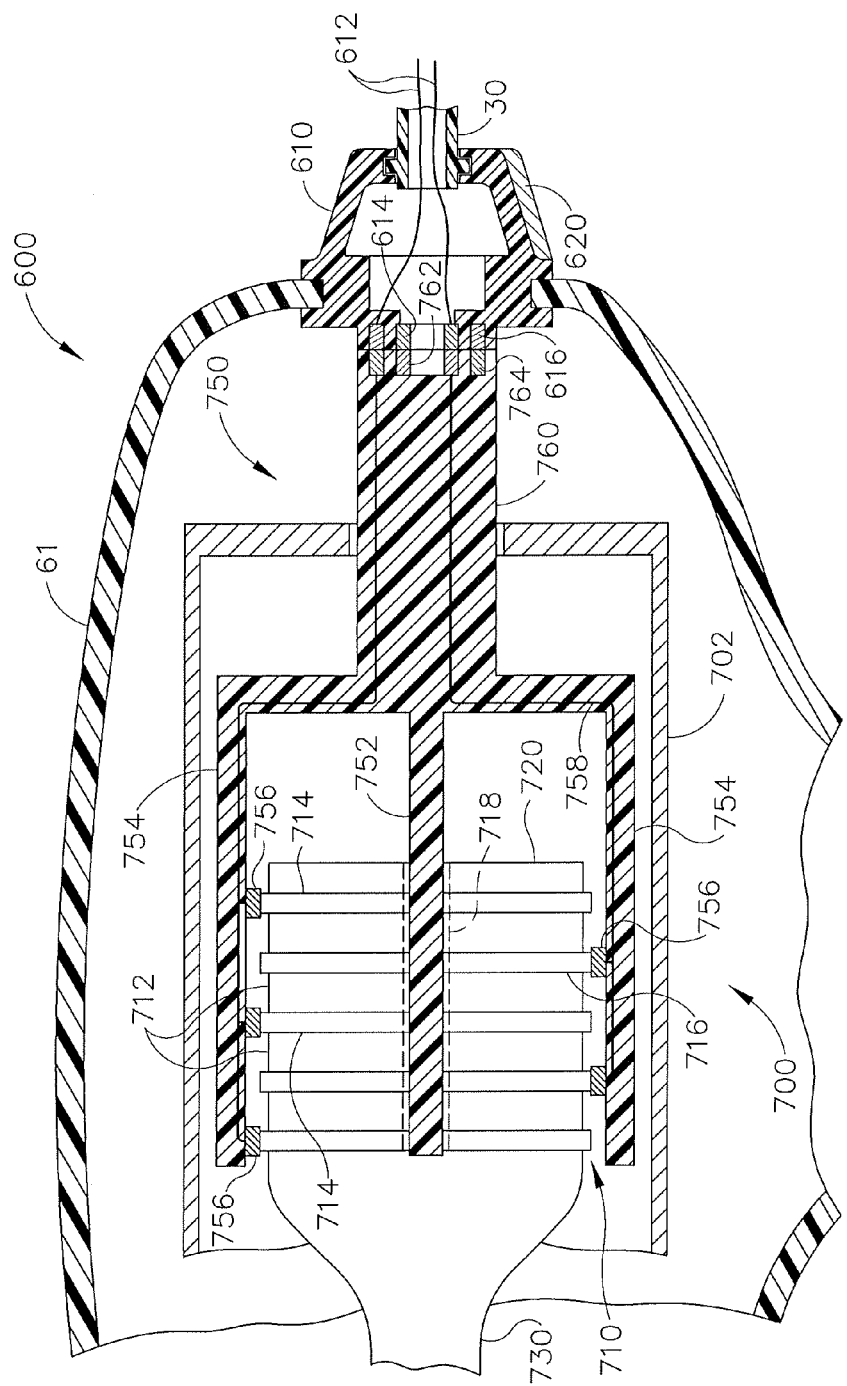
FIG. 8 depicts an enlarged side cross-sectional view of an exemplary alternative connection assembly having a cable end with a weighted portion coupled to a ring contact connection.

One merely exemplary configuration for such a rotatable connection assembly (600) is shown in FIG. 8. In the example shown, cable (30) includes one or more wires (612) extending to a cable end (610) that is rotatably coupled to a transducer (700) such that cable (30), cable end (610), transducer (700), and/or casing (61) are rotatable relative to each other. Cable end (610) will be discussed in more detail below. Transducer (700) of the present example may be constructed in accordance with at least some of the teachings of transducer (100) described above. In the example shown, transducer (700) comprises an outer casing (702), a piezo stack assembly (710), a first resonator or end-bell (720), and a second resonator or fore-bell (730). In the present example, ultrasonic energy produced by transducer (700) is transmitted to blade (82) of end effector (80) via waveguide (76) (shown in FIGS. 1-2). Waveguide (76) is coupled at a proximal end to a horn (not shown) extending distally from second resonator (730). The horn may be fixedly coupled to waveguide (76) (such that rotation of transmission assembly (70) rotates transducer (700) and vice versa) or the horn may be configured to rotate freely relative to waveguide (76) (such that rotation of transmission assembly (70) is independent of transducer (700)).

In the example shown, piezo stack assembly (710) comprises a plurality of piezoelectric elements (712) that are compressed between first resonator (720) and second resonator (730) to form a stack of piezoelectric elements (712) when first resonator (720) and second resonator (730) are assembled with piezoelectric elements (712). Piezoelectric elements (712) may be fabricated from any suitable material, for example, lead zirconate-titanate, lead meta-niobate, lead titanate, and/or any suitable piezoelectric crystal material, for example. Piezo stack assembly (710) further comprises a plurality of electrodes (714, 716), including at least one positive electrode (714) and at least one negative electrode (716) that are configured to create a voltage potential across the one or more piezoelectric elements (712). As shown in FIG. 8, a plurality of electrodes (714, 716) and piezoelectric elements (712) are stacked between first and second resonators (720, 730). Additionally, positive electrodes (714), negative electrodes (716), and piezoelectric elements (712) further comprise a bore (718) (shown in phantom) that defines a passageway to receive a threaded portion of first resonator (720) and/or a shaft (752) of a first slip ring structure (750), as will be described in more detail below. For instance, the shaft (752) may be coaxial and insertable within a hollow threaded portion of first resonator (720), which is threaded into bore (718). Bore (718) thus permits piezo stack assembly (710), first resonator (720), and second resonator (730) to translate and/or rotate relative to shaft (752). In the present example, positive electrodes (714) and negative electrodes (716) are annular rings, though it should be understood that other electrodes may be used, such as linear tabs and/or any other suitable electrode or combination of electrodes as will be apparent to one of ordinary skill in the art in view of the teachings herein.

When transducer (700) of the present example is activated via toggle button (69) and/or trigger (68) (shown in FIG. 2), transducer (700) is operable to create mechanical energy in the form of linear oscillations or vibrations (e.g., torsional or transverse, etc.), at an ultrasonic frequency (such as 55.5 kHz). Accordingly, when transducer (700) is coupled to transmission assembly (70), then the oscillations are transmitted through waveguide (76) to end effector (80). Blade (82), being coupled to waveguide (76), thereby oscillates at the ultrasonic frequency. Thus, when tissue is secured between blade (82) and clamp arm (84), the ultrasonic oscillation of blade (82) may simultaneously sever the tissue and denature the proteins in adjacent tissue cells, thereby providing a coagulative effect with relatively little thermal spread. An electrical current may also be provided through blade (82) and clamp arm (84) to also cauterize the tissue. While some configurations for transducer (700) have been described, still other suitable configurations for transducer (700) will be apparent to one or ordinary skill in the art in view of the teachings herein.

First slip ring structure (750) of the present example is configured to electrically couple wires (612) of cable (30) to positive electrodes (714) and negative electrodes (716) while permitting rotation of piezo stack assembly (710), first resonator (720), and second resonator (730) relative to cable (30). Such rotation of piezo stack assembly (710), first resonator (720), and second resonator (730) may be accomplished using a rotation knob, such as rotation knob (66) shown in FIGS. 1-2, or by any other suitable means. In the present example, first slip ring structure (750) is supported by roller bearing assemblies (not shown) configured to permit first slip ring structure (750) to rotate relative to casing (610). First slip ring structure (750) comprises a shaft (752) (as noted previously), one or more bars (754), and one or more brush contacts (756) configured to electrically couple to positive and/or negative electrodes (714, 716). In the example shown, a pair of bars (754) are L-shaped and located on opposing sides of electrodes (714, 716), though it should be understood that a single, straight or L-shaped, bar (754) may be used or, alternatively, multiple bars (754), such as three, four, five, or six bar configurations, may be used as well. Shaft (752) and bars (754) of the present example comprise a non-conductive or insulating material such that brush contacts (756) do not electrically couple to shaft (752) or bars (754). Brush contacts (756) are configured to electrically couple to positive and/or negative electrodes (714, 716) to provide power to piezo stack assembly (710). Brush contacts (756) may be made from copper, aluminium, gold, and/or any other suitable conductive material. In the example shown, one bar (754) comprises a plurality of positive brush contacts (756) while a second bar (754) comprises a plurality of negative brush contacts (756), though it should be understood that this is merely optional. In the instance where a single bar (754) is used, all brush contacts (756) may be included on that single bar (754). Brush contacts (756) may optionally further be configured in accordance with the connection assemblies (200, 300, 400, 500) described above. First slip ring structure (750) further comprises conductive paths (758) electrically coupling brush contacts (756) to a corresponding ring contact (762, 764), described in more detail below. Conductive paths (758) may be wires extending along or through first slip ring structure (750) or conductive paths (758) may be etched into first slip ring structure (750) in a similar fashion to a PCB.

A proximal shaft (760) extends proximally from shaft (752) and is fixedly attached to bars (754) such that shaft (752), proximal shaft (760), and bars (754) form a unitary structure. Of course, proximal shaft (760) may be omitted and shaft (752) may extend proximally of the intersection of bars (754). At the proximal end of proximal shaft (760) is a pair of ring contacts (762, 764) that are each electrically coupled to a respective conductive path (758). In the example shown, a positive ring contact (762) is electrically coupled those brush contacts (756) that are electrically coupled to positive electrodes (714), and a negative ring contact (764) is electrically coupled to those brush contacts (756) that are electrically coupled to negative electrodes (716). In the example shown, positive ring contact (762) is coaxial to, and nested within, negative ring contact (764). Ring contacts (762, 764) electrically couple to complementary ring contacts (614, 616) within cable end (610) such that wires (612) are electrically coupled to corresponding conductive paths (758). One merely exemplary connection is a slip ring connection. Thus, wires (612) and conductive paths (758) remain electrically coupled even if first slip ring structure (750) rotates relative to cable end (32). Furthermore, cable end (610) comprises a weighted portion (620) configured to orient cable end (610) with weighted portion (620) substantially pointed downwardly due to the force of gravity. In the present example, weighted portion is located substantially on a lower portion, or side, of cable end (610). Thus, even if first slip ring structure (750) rotates relative to cable end (610), weighted portion (620) substantially maintains cable (30) in its original position, thereby reducing the possibility of tangling of cable (30) as transducer (700) and/or surgical instrument (50) is rotated. Slip ring structure (750) may alternatively be contained within a mid-housing (not shown) that is rotatable relative to transducer (700) and is located between transducer (700) and cable end (610). Slip ring structure (750) may also be designed to be included in the acoustic configuration of transducer (700) such that slip ring structure (750) does not affect the oscillatory motion produced by transducer (700). In another alternative, first slip ring structure (750) may be secured and electrically coupled to positive and/or negative electrodes (714, 716) such that transducer (700) is unitarily constructed. Of course, still other configurations for rotatable connection assembly (600) will be apparent to one of ordinary skill in the art in view of the teachings herein.

H. Exemplary Selectively Coupleable Slip Ring

While the preceding discussion related to a rotatable connection assembly, in other instances it may be useful to provide a selectively coupleable electrical connection from cable (30) to transducer (100). In the instances when transducer (100) must be rotated multiple times during an operation, if cable (30) is fixed relative to transducer (100), then cable (30) may wind around unnecessarily. As an alternative to a rotatable electrical connection, it may be preferable to selectively decouple at least part of the cable end from transducer (100) while casing (61) and the cable end are still physically coupled. Accordingly, it may be preferable to include a selectively coupleable electrical connection between the cable end and transducer (100) to selectively relieve any twisting in cable (30). One merely exemplary configuration for such selectively coupleable electrical connection is described below.

Figure 9A:
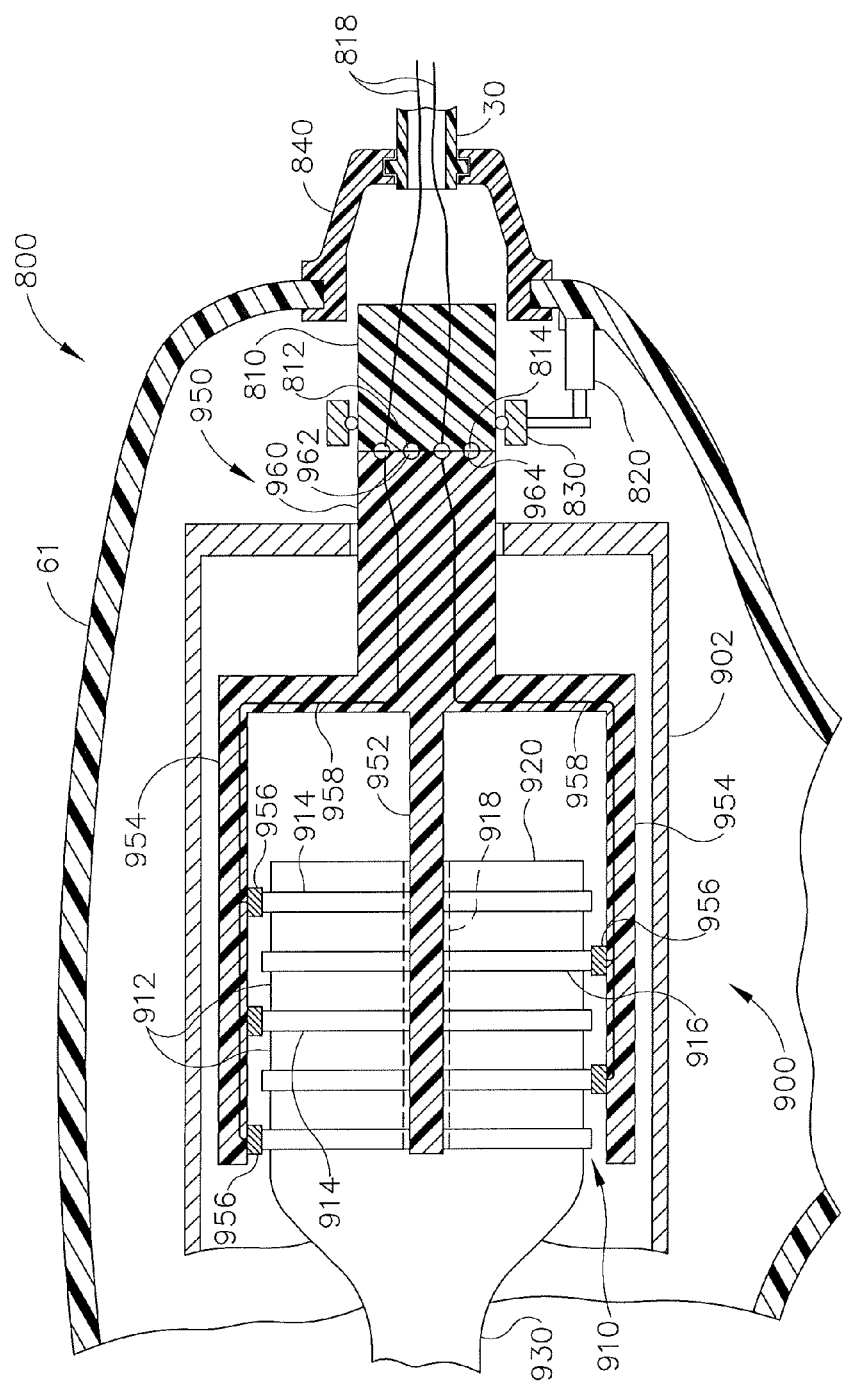
FIG. 9A depicts an enlarged side cross-sectional view of yet another exemplary alternative connection assembly having a selectively coupleable member.
Figure 9B:
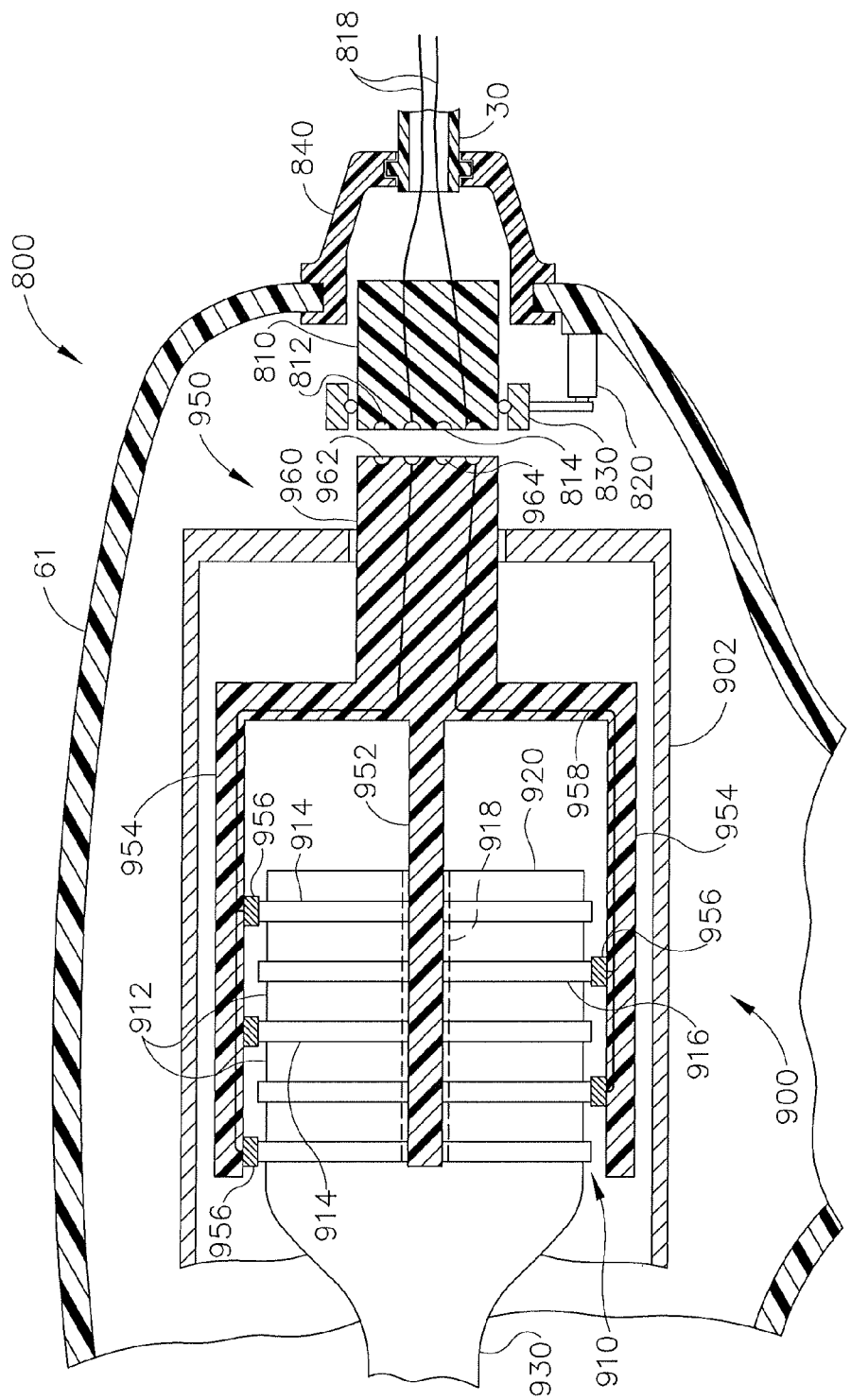
FIG. 9B depicts an enlarged side cross-sectional view of the connection assembly of FIG. 9A showing the coupleable member decoupled.

As shown in FIGS. 9A-9B, an alternative coupleable connection assembly (800) is shown selectively connecting cable (30) to a transducer (900). In the present example, transducer (900) is configured substantially in accordance with the teachings of transducer (700). In the example shown, transducer (900) comprises an outer casing (902), a piezo stack assembly (910), a first resonator or end-bell (920), and a second resonator or fore-bell (930). In the present example, ultrasonic energy produced by transducer (900) is transmitted to blade (82) of end effector (80) via waveguide (76) (shown in FIGS. 1-2). Waveguide (76) is coupled at a proximal end to a horn (not shown) extending distally from second resonator (930). The horn may be fixedly coupled to waveguide (76) (such that rotation of transmission assembly (70) rotates transducer (900) and vice versa) or the horn may be configured to rotate freely relative to waveguide (76) (such that rotation of transmission assembly (70) is independent of transducer (900)).

In the example shown, piezo stack assembly (910) comprises a plurality of piezoelectric elements (912) that are compressed between first resonator (920) and second resonator (930) to form a stack of piezoelectric elements (912) when first resonator (920) and second resonator (930) are assembled with piezoelectric elements (912). Piezoelectric elements (912) may be fabricated from any suitable material, for example, lead zirconate-titanate, lead meta-niobate, lead titanate, and/or any suitable piezoelectric crystal material, for example. Piezo stack assembly (910) further comprises a plurality of electrodes (914, 916), including at least one positive electrode (914) and at least one negative electrode (916) that are configured to create a voltage potential across the one or more piezoelectric elements (912). As shown in FIG. 9A-9B, a plurality of electrodes (914, 916) and piezoelectric elements (912) are stacked between first and second resonators (920, 930). Additionally, positive electrodes (914), negative electrodes (916), and piezoelectric elements (912) further comprise a bore (918) (shown in phantom) to define a passageway to receive a threaded portion of first resonator (920) and/or a shaft (952) of a first slip ring structure (950), as will be described in more detail below. For instance, the shaft (952) may be coaxial and insertable within a hollow threaded portion of first resonator (920), which is threaded into bore (918). Bore (918) thus permits piezo stack assembly (910), first resonator (920), and second resonator (930) to translate and/or rotate relative to shaft (952). In the present example, positive electrodes (914) and negative electrodes (916) are annular rings, though it should be understood that other electrodes may be used, such as linear tabs and/or any other suitable electrode or combination of electrodes as will be apparent to one of ordinary skill in the art in view of the teachings herein.

When transducer (900) of the present example is activated via toggle button (69) and/or trigger (68) (shown in FIG. 2), transducer (900) is operable to create mechanical energy in the form of linear oscillations or vibrations (or other vibrational modes, e.g., torsional or transverse, etc.), at an ultrasonic frequency (such as 55.5 kHz). Accordingly, when transducer (900) is coupled to transmission assembly (70), then the oscillations are transmitted through waveguide (76) to end effector (80). Blade (82), being coupled to waveguide (76), thereby oscillates at the ultrasonic frequency. Thus, when tissue is secured between blade (82) and clamp arm (84), the ultrasonic oscillation of blade (82) may simultaneously sever the tissue and denature the proteins in adjacent tissue cells, thereby providing a coagulative effect with relatively little thermal spread. An electrical current may also be provided through blade (82) and clamp arm (84) to also cauterize the tissue. While some configurations for transducer (900) have been described, still other suitable configurations for transducer (900) will be apparent to one or ordinary skill in the art in view of the teachings herein.

First slip ring structure (950) of the present example is configured to electrically couple wires (818) of cable (30) to positive electrodes (914) and negative electrodes (916) while permitting rotation of piezo stack assembly (910), first resonator (920), and second resonator (930) relative to cable (30). Such rotation of piezo stack assembly (910), first resonator (920), and second resonator (930) may be accomplished using a rotation knob, such as rotation knob (66) shown in FIGS. 1-2, or by any other suitable means. First slip ring structure (950) comprises a shaft (952) (as noted previously), one or more bars (954), and one or more brush contacts (956) configured to electrically couple to positive and/or negative electrodes (914, 916). In the example shown, a pair of bars (954) are L-shaped and located on opposing sides of electrodes (914, 916), though it should be understood that a single, straight or L-shaped, bar (954) may be used or, alternatively, multiple bars (954), such as three, four, five, or six bar configurations, may be used as well. Shaft (952) and bars (954) of the present example comprise a non-conductive or insulating material such that brush contacts (956) do not electrically couple to shaft (952) or bars (954). Brush contacts (956) are configured to electrically couple to positive and/or negative electrodes (914, 916) to provide power to piezo stack assembly (910). Brush contacts (956) may be made from copper, aluminium, gold, and/or any other suitable conductive material. In the example shown, one bar (954) comprises a plurality of positive brush contacts (956) while a second bar (954) comprises a plurality of negative brush contacts (956), though it should be understood that this is merely optional. In the instance where a single bar (954) is used, all brush contacts (956) may be included on that single bar (954). Brush contacts (956) may optionally further be configured in accordance with the connection assemblies (200, 300, 400, 500) described above. First slip ring structure (950) further comprises conductive paths (958) electrically coupling brush contacts (956) to a corresponding contact (962, 964) that may be electrically coupled to coupleable member (810), described in more detail below. Conductive paths (958) may be wires extending along or through first slip ring structure (950) or conductive paths (958) may be etched into first slip ring (950) structure in a similar fashion to a PCB.

A proximal shaft (960) extends proximally from shaft (952) and is fixedly attached to bars (954) such that shaft (952), proximal shaft (960), and bars (954) form a unitary structure. Of course, proximal shaft (960) may be omitted and shaft (952) may extend proximally of the intersection of bars (954). At the proximal end of proximal shaft (960) is a pair of contacts (962, 964) that are each electrically coupled to a respective conductive path (958). In the example shown, a positive contact (962) is electrically coupled those brush contacts (956) that are electrically coupled to positive electrodes (914), and a negative contact (964) is electrically coupled to those brush contacts (956) that are electrically coupled to negative electrodes (916). In one example, positive contact (962) is an annular contact coaxial to, and nested within, negative contact (964), which is also an annular contact. Complementary annular contacts (812, 814) are provided on coupleable member (810) to electrically couple to positive and negative contacts (962, 964). Alternatively, male connectors and complementary female connectors may be used as an alternative to annular ring contacts (962, 964, 812, 814).

In some instances, the rotation of transducer (900), casing (61), and/or cable (30) may cause wires (818) to twist about one another. Accordingly, a solenoid (820) and a bearing member (830) disposed about coupleable member (810) and translatable relative to proximal shaft (960) are provided to selectively decouple positive and negative contacts (962, 964) and complementary annular contacts (812, 814). Bearing member (830) allows coupleable member (810) to rotate relative to casing (61) when coupleable member (810) is decoupled from proximal shaft (960). It should be understood that cable end (840) may be permitted to rotate freely relative to casing (61) regardless of whether coupleable member (810) is coupled to proximal shaft (960). As shown in FIG. 9A, solenoid (820) is active and extended, which causes positive and negative contacts (962, 964) and complementary annular contacts (812, 814) to be electrically coupled when coupleable member (810) abuts proximal shaft (960). When solenoid (820) is inactive, as shown in FIG. 9B, coupleable member (810) is translated proximally such that positive and negative contacts (962, 964) and complementary annular contacts (812, 814) are decoupled. With coupleable member (810) disposed within bearing member (830), wires (818) may be permitted to untwist while coupleable member (810) rotates within bearing member (830). In the example shown, connection assembly (800) is configured to be in the first position, shown in FIG. 9A, when trigger (68) is actuated, and such that connection assembly (800) moves to the second position, shown in FIG. 9B, when trigger (68) (shown in FIGS. 1-2) is released by the user. Such activation may be accomplished through a switch (not shown) to selectively apply power to solenoid (820) based upon the position of trigger (68). Accordingly, power may be selectively applied to transducer (100) when the user actuates trigger (68) via the coupling of positive and negative contacts (962, 964) with complementary annular contacts (812, 814). Alternatively, solenoid (820) may be activated by toggle button (69) (shown in FIG. 2) and/or by any other activation device as will be apparent to one of ordinary skill in the art in view of the teachings herein.

Of course, solenoid (820) may alternatively be configured so that when solenoid (820) is active, then coupleable member (810) is decoupled, and when solenoid (820) is inactive, then coupleable member (810) is recoupled to proximal shaft (960). Further still, proximal shaft (960) may be configured to form the core of a solenoid with a selectively electrically activated coil (not shown) disposed about proximal shaft (960). Accordingly, when the coil is activated, proximal shaft (960) translates to couple or decouple from engagement with coupleable member (810). Yet another version may omit solenoid (820) and coupleable member (810) may be mechanically actuated by the actuation of trigger (68) and/or trigger assembly (150) described above, such as through a clutch assembly. For instance, a second intermediate member (not shown) may mechanically link bearing member (830) to trigger assembly (150).

In yet a further alternative, coupleable member (810) and proximal shaft (960) may each comprise a magnet such that coupleable member (810) and proximal shaft (960) are magnetically held together. Solenoid (820), a motor, or a direct mechanical coupling from trigger (68) may be configured to drive a wedge between coupleable member (810) and proximal shaft (960) to decouple the magnetic coupling of coupleable member (810) and proximal shaft (960). In some versions the magnets may be omitted and resiliently biased springs may be used to compress coupleable member (810) and proximal shaft (960) together. In other versions, the wedge may be omitted and a pressure bladder or second solenoid may be positioned between flanges on both coupleable member (810) and proximal shaft (960). Accordingly, when the bladder is inflated or the second solenoid is activated, coupleable member (810) and proximal shaft (960) are driven outwardly to decouple coupleable member (810) and proximal shaft (960). In some versions, the flange on coupleable member (810) may be affixed to casing (902) such that only proximal shaft (960) is translated relative to casing (902). In some other versions the flange on proximal shaft (960) may be affixed to casing (902). Still further configurations for proximal shaft (960) and coupleable member (810) will be apparent to one of ordinary skill in the art in view of the teachings herein. Moreover, while coupleable connection assembly (800) is shown within outer casing (902) of transducer (900), it should be understood that coupleable connection assembly (800) may be disposed within a cable end (840) or disposed between transducer (900) and cable end (840).

Still other configurations for coupleable connection assembly (800) will be apparent to those of ordinary skill in the art in view of the teachings herein. For instance, in one merely exemplary alternative, coupleable member (810) and proximal shaft (960) may comprise a selectively locking slip ring assembly. In such a version, solenoid (820) may be operable to selectively apply one or more frictional pads to proximal shaft (960) and/or coupleable member (810), thereby preventing rotation of proximal shaft (960) and/or coupleable member (810) relative to the other. Such braking on proximal shaft (960) and/or coupleable member (810) may be applied when the user actuates trigger (68), but is released when trigger (68) is no longer actuated. Accordingly, when the braking provided by solenoid (820) is not applied, coupleable member (810) may rotate freely relative to transducer (900), casing (610), cable (30), and/or cable end (840), thereby allowing wires (816) to substantially unwind and/or untangle. Of course solenoid (820) may be omitted from the foregoing examples and a mechanical linkage may be provided from trigger (68) instead.

While certain configurations of exemplary surgical instruments have been described, various other ways in which the surgical instruments may be configured will be apparent to those of ordinary skill in the art in view of the teachings herein. By way of example only, the surgical instruments referred to herein may be constructed in accordance with at least some of the teachings of U.S. Pat. No. 6,500,176; U.S. Pat. No. 6,783,524; U.S. Pat. No. 7,416,101; U.S. Pat. No. 7,738,971; U.S. Pat. No. 6,783,524; U.S. Pub. No. 2006/0079874; U.S. Pub. No. 2007/0191713; U.S. Pub. No. 2007/0282333; U.S. Pub. No. 2008/0200940; U.S. Pub. No. 2009/0209990, issued as U.S. Pat. No. 8,657,174; U.S. Pub. No. 2010/0069940, issued as U.S. Pat. No. 9,023,071; and/or U.S. Provisional Application Serial No. 61/410,603.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery. For instance, those of ordinary skill in the art will recognize that various teaching herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical system comprising:
   (a) a connector configured to couple with a power supply, wherein the connector comprises a first wire; and
   (b) a surgical instrument coupled to the connector, the surgical instrument comprising:
      (i) a body assembly,
      (ii) a transducer associated with the body assembly, the transducer comprising:
         (1) a first electrode, and
         (2) a transducer element in communication with the first electrode, and
      (iii) a connection assembly operable to selectively electrically couple the first wire to the first electrode, wherein the connection assembly comprises:
         (1) an extensible member,
         (2) a driving feature, wherein the driving feature is operable to drive the extensible member from a retracted position to an extended position, wherein the extensible member is configured to couple the first wire with the first electrode in the extended position, and
         (3) a guidance feature configured to direct the extensible member toward the first electrode as the extensible member is driven from the retracted position to the extended position.

2. The surgical system of claim 1, wherein the body assembly further comprises a trigger.

3. The surgical system of claim 2, wherein the trigger is operable to actuate the connection assembly.

4. The surgical system of claim 1, wherein the driving feature comprises a solenoid, wherein the solenoid is operable to extend the extensible member relative to the guidance feature to contact the first electrode.

5. The surgical system of claim 4, wherein the connector further comprises a second wire, wherein the transducer further comprises a second electrode, wherein the connection assembly comprises a first extensible member and a second extensible member, wherein the solenoid is operable to extend the first extensible member to contact the first electrode and to extend the second extensible member to contact the second electrode.

6. The surgical system of claim 5 wherein the first extensible member and the second extensible member comprise resilient members.

7. The surgical system of claim 5, wherein the first extensible member is electrically coupled to the first wire and the second extensible member is electrically coupled to the second wire.

8. The surgical system of claim 4 wherein the guidance feature comprises a redirection member comprising a passageway having an entrance at a first angle relative to the redirection member and an exit at a second angle relative to the redirection member, wherein the first angle and the second angle are different angles.

9. The surgical system of claim 8 wherein second angle is 90 degrees relative to the first angle.

10. The surgical system of claim 1, wherein the connector further comprises a second wire, wherein the transducer further comprises a second electrode, wherein the connection assembly comprises a solenoid, a frame, and a contact, wherein the frame comprises an end plate, wherein the contact is coupled to a first end of the solenoid, wherein the solenoid is operable to extend the contact into engagement with the first electrode or the second electrode such that the first electrode or the second electrode is located between the contact and the end plate, and wherein the contact is electrically coupled to the first wire or the second wire.

11. The surgical system of claim 10 wherein the connection assembly comprises a first contact and a second contact, wherein the frame comprises a first end plate and a second end plate, wherein the first contact is coupled to a first end of the solenoid, wherein the second contact is coupled to a second end of the solenoid, wherein the solenoid is operable to extend the first contact into engagement with the first electrode and to extend the second contact into engagement with the second electrode, and wherein the first contact is electrically coupled to the first wire and the second contact is electrically coupled to the second wire.

12. The surgical system of claim 1, wherein the connector further comprises a second wire, wherein the transducer further comprises a second electrode, wherein the connection assembly comprises solenoid and a frame, wherein the frame comprises a first contact and a second contact, wherein a first end of the solenoid is coupled to the frame, wherein the solenoid is operable to translate the frame such that the first contact or the second contact is electrically coupled with the first electrode or the second electrode, and wherein the first contact is electrically coupled to the first wire and the second contact is electrically coupled to the second wire.

13. The surgical system of claim 12 wherein the solenoid is operable to translate the frame such that the first contact is electrically coupled to the first electrode and the second contact is electrically coupled to the second electrode.

14. The surgical system of claim 1, wherein the surgical instrument further comprises a transmission assembly extending distally from the body assembly.

15. The surgical system of claim 14, wherein the transmission assembly comprises a waveguide and a blade, wherein the waveguide further comprises a proximal end and a distal end, wherein the blade is located at the distal end of the waveguide, wherein the transducer is coupleable with the waveguide.

16. The surgical system of claim 1, wherein the first electrode and the transducer element are rotatable relative to the body assembly.

17. The surgical system of claim 1, wherein the extensible member is electrically coupled to the first wire.

18. The surgical system of claim 1, further comprising a power supply, wherein the connector is configured to couple with the power supply.

19. The surgical system of claim 18 wherein the power supply and the connector are within the body assembly.

20. The surgical system of claim 18 wherein the power supply comprises a generator.

21. The surgical system of claim 20, wherein the generator is separate from the surgical instrument.

\* \* \* \* \*